(12) United States Patent
Hull et al.

(10) Patent No.: US 8,806,950 B2
(45) Date of Patent: Aug. 19, 2014

(54) ELECTROMAGNETIC ACOUSTIC TRANSDUCER SYSTEM

(75) Inventors: John Ralph Hull, Sammamish, WA (US); Michael Strasik, Sammamish, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 308 days.

(21) Appl. No.: 13/292,594

(22) Filed: Nov. 9, 2011

(65) Prior Publication Data

US 2013/0111998 A1 May 9, 2013

(51) Int. Cl.
*G01N 29/04* (2006.01)

(52) U.S. Cl.
USPC .............................................. 73/643; 73/578

(58) Field of Classification Search
USPC ............ 73/643, 578, 597, 632, 641; 324/221, 324/222
See application file for complete search history.

(56) References Cited

U.S. PATENT DOCUMENTS

| | | | |
|---|---|---|---|
| 4,278,881 A | | 7/1981 | Mann |
| 4,395,913 A | * | 8/1983 | Peterson ........................ 73/643 |
| 4,777,824 A | * | 10/1988 | Alers et al. ..................... 73/643 |
| 5,059,902 A | * | 10/1991 | Linder ..................... 324/207.17 |
| 5,187,435 A | | 2/1993 | Geweke |
| 5,689,070 A | * | 11/1997 | Clark et al. ..................... 73/643 |
| 5,721,379 A | * | 2/1998 | Palmer et al. ................... 73/643 |
| 5,929,723 A | * | 7/1999 | Kimura et al. ................. 333/193 |
| 5,936,162 A | * | 8/1999 | Lingenberg et al. ............ 73/643 |
| 5,987,993 A | * | 11/1999 | Meier et al. ..................... 73/643 |
| 6,025,769 A | * | 2/2000 | Chu et al. ....................... 335/216 |
| 6,465,739 B1 | * | 10/2002 | Shepherd et al. .......... 174/125.1 |
| 6,541,963 B2 | | 4/2003 | Mednikov et al. |
| 7,917,255 B1 | * | 3/2011 | Finley ................................ 701/9 |

FOREIGN PATENT DOCUMENTS

EP 0067065 A1 12/1982

OTHER PUBLICATIONS

Hull et al., "Applications of Bulk High-Temperature Superconductors", Proceedings of the IEEE, vol. 92, No. 10, Oct. 2004, pp. 1705-1718.
UK search report dated Feb. 12, 2013 regarding application GB1219937.8, Reference P56009GB, applicant The Boeing Company, 6 pages.

* cited by examiner

*Primary Examiner* — J M Saint Surin
(74) *Attorney, Agent, or Firm* — Yee & Associates, P.C.

(57) ABSTRACT

A method and apparatus for an electromagnetic acoustic transducer. An apparatus comprises a conductive material and a current inducer. The conductive material is configured to generate a magnetic field, wherein the magnetic field has magnetic flux lines that are substantially fixed and the conductive material has a temperature that is equal to or less than a critical temperature at which the conductive material has substantially zero electrical resistance. The current inducer is configured to cause an electric current to flow in a test object that interacts with the magnetic field, wherein the electric current has a frequency that generates an acoustic wave in the test object.

21 Claims, 8 Drawing Sheets

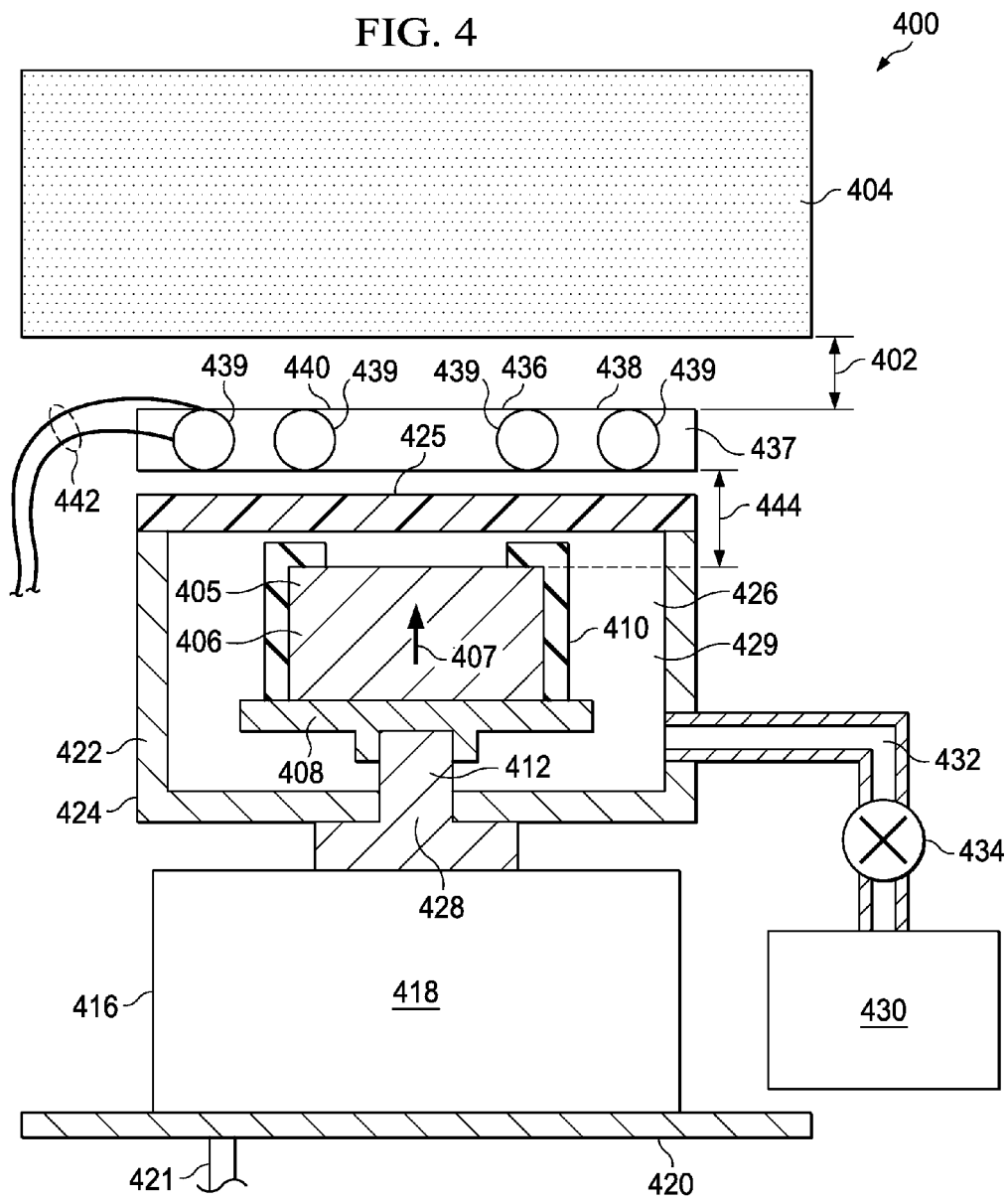

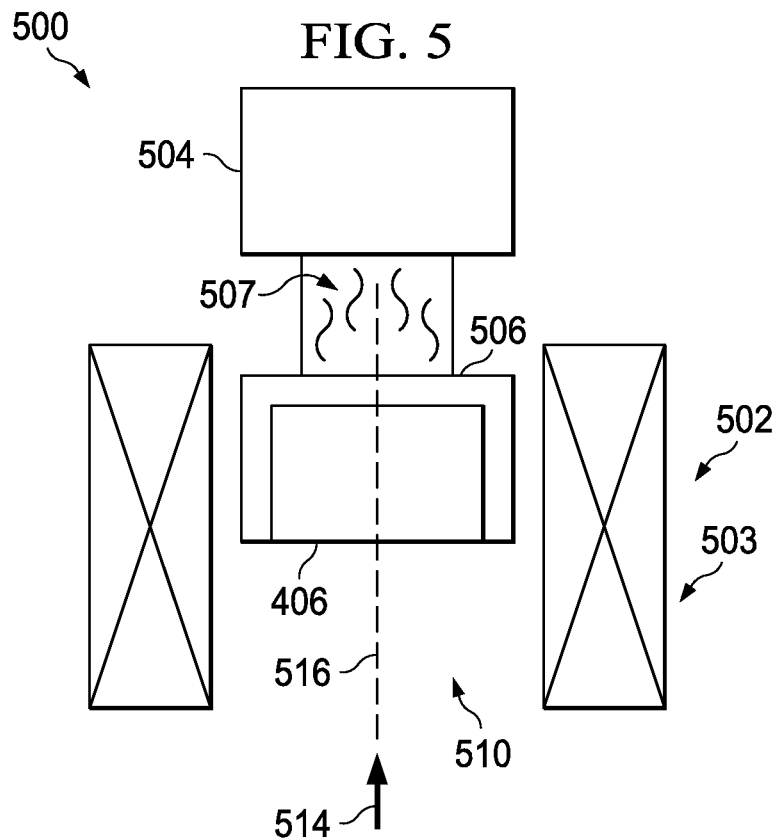
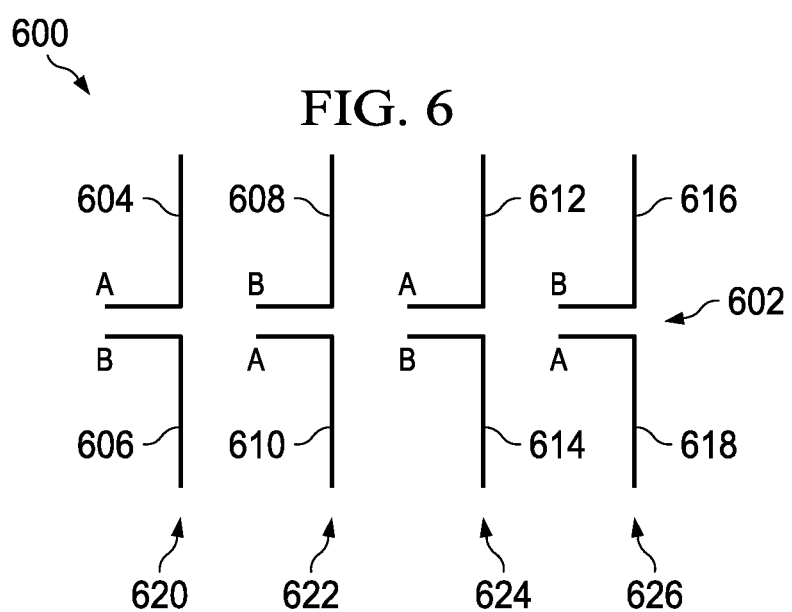

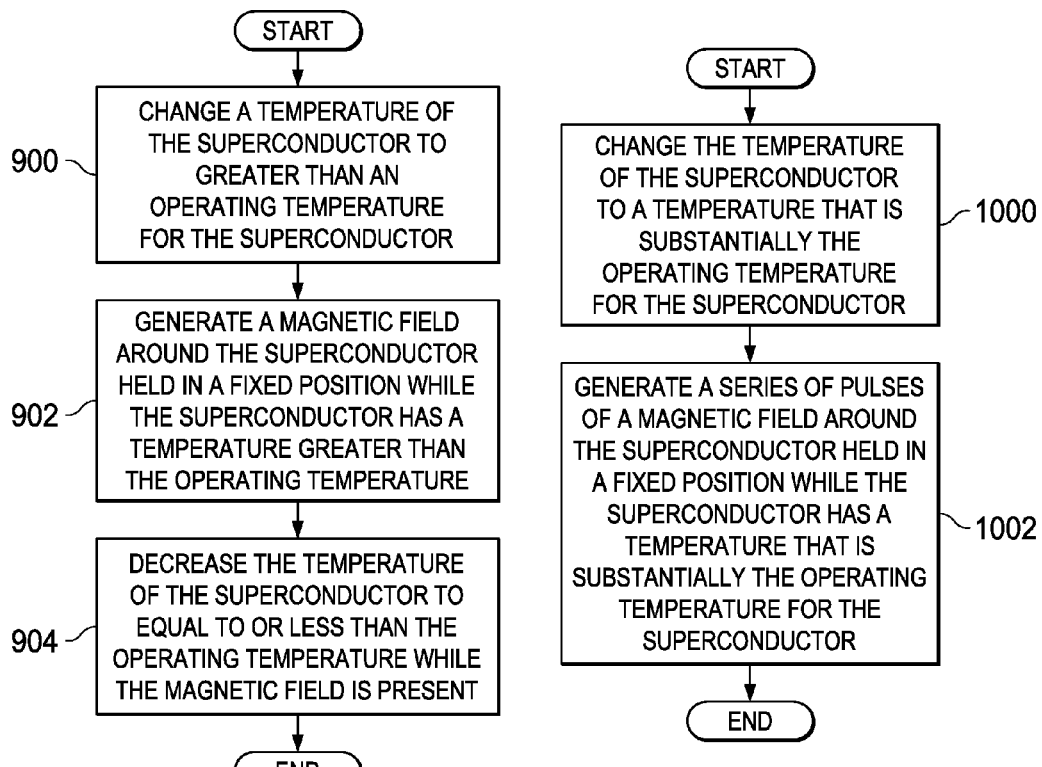
FIG. 9
FIG. 10
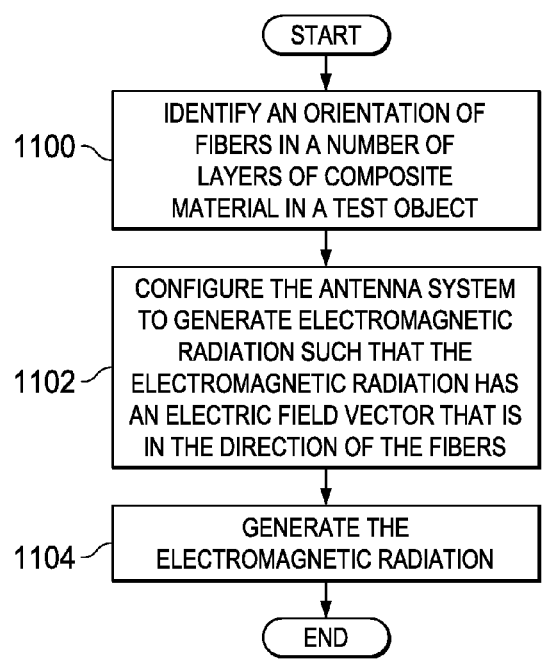
FIG. 11

ELECTROMAGNETIC ACOUSTIC TRANSDUCER SYSTEM

BACKGROUND INFORMATION

1. Field

The present disclosure relates generally to inspecting objects and, in particular, to performing non-destructive inspection of objects.

2. Background

When objects are manufactured or assembled, it is often desirable to determine whether those objects meet different requirements. For example, when parts are welded to each other, a determination may be made as to whether inconsistencies are present in the weld. As another example, in manufacturing objects such as skin panels, spars, and other structures from composite materials, it is often desirable to determine whether inconsistencies are present in the objects. Inconsistencies may take the form of voids, delaminations, and other types of inconsistencies.

In testing these objects, it is often desirable to perform tests without permanently changing the objects. For example, cutting or performing other tests that may change the objects on a permanent basis is undesirable because these changes may render the objects unusable.

Non-destructive inspection is a type of testing that does not permanently alter an object in an undesired manner. In other words, the object may still be used for its intended purpose after non-destructive inspection of the object. Non-destructive inspection may include ultrasonic testing, x-ray testing, visual inspection, eddy current testing, and other suitable types of testing.

With ultrasonic testing, transducers are used to generate and detect acoustic waves in an object. These transducers often take the form of piezoelectric transducers.

With this type of transducer, the transducer is placed in contact with the object being tested. The transducer is typically coupled to the test object by a coupling medium. This coupling medium may be, for example, water, oil, or some other suitable medium.

The transducer generates acoustic waves in the test object. A response to the acoustic waves is received by the transducer. This response is analyzed to perform the inspection. In particular, the response may be analyzed to determine whether any inconsistencies are present in the test object.

In some cases, contact between the transducer and the test object may be undesirable. Further, the use of a coupling medium also may be undesirable.

In these cases, an electromagnetic acoustic transducer (EMAT) may be used in place of traditional piezoelectric transducers. Electromagnetic acoustic transducers may be particularly useful for automated inspections and inspections in hot and cold environments.

An electromagnetic acoustic transducer may be used both to generate acoustic waves and detect responses to the acoustic waves. An electromagnetic acoustic transducer uses an electromagnetic mechanism to generate the acoustic waves. With this type of transducer, a coupling medium may be unnecessary.

Electromagnetic acoustic transducers, however, may not be ideal for all types of materials and test objects. For example, materials that have low conductivity may not be ideal candidates for testing with electromagnetic acoustic transducers. Electromagnetic acoustic transducers may not operate at as large a stand-off distance as desired or may not detect inconsistencies as small as desired.

Therefore, it would be advantageous to have a method and apparatus that takes into account at least some of the issues discussed above, as well as possibly other issues.

SUMMARY

In one advantageous embodiment, an apparatus comprises a conductive material and a current inducer. The conductive material is configured to generate a magnetic field, wherein the magnetic field has magnetic flux lines that are substantially fixed and wherein the conductive material has a temperature that is equal to or less than a critical temperature at which the conductive material has substantially zero electrical resistance. The current inducer is configured to cause an electric current to flow in a test object that interacts with the magnetic field, wherein the electric current has a frequency that generates an acoustic wave in the test object.

In another advantageous embodiment, a method for operating an electromagnetic acoustic transducer is present. The electromagnetic acoustic transducer is positioned relative to a test object, wherein a conductive material is configured to generate a magnetic field that encompasses at least a portion of the test object. The magnetic field has magnetic flux lines that are substantially fixed. The conductive material has a temperature that is equal to or less than a critical temperature at which the conductive material has substantially zero electrical resistance. The electromagnetic acoustic transducer causes an electric current to flow in the portion of the test object encompassed by the magnetic field. The electric current interacts with the magnetic field to generate an acoustic wave in the test object.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof will best be understood by reference to the following detailed description of an advantageous embodiment of the present disclosure when read in conjunction with the accompanying drawings, wherein:

FIG. 4 is an illustration of a cross-sectional view of an electromagnetic acoustic transducer in accordance with an advantageous embodiment;

FIG. 5 is an illustration of an implementation for a magnetic field and production environment in accordance with an advantageous embodiment;

FIG. 6 is an illustration of an antenna in accordance with an advantageous embodiment;

FIG. 9 is an illustration of a flowchart of a process for preparing a superconductor for use in an electromagnetic acoustic transducer in accordance with an advantageous embodiment;

FIG. 10 is an illustration of a flowchart of a process for preparing a superconductor for use in an electromagnetic acoustic transducer in accordance with an advantageous embodiment;

FIG. 11 is an illustration of a flowchart of a process for generating an acoustic wave in a composite material in accordance with an advantageous embodiment;

DETAILED DESCRIPTION

The different advantageous embodiments recognize and take into account that most currently used magnets for electromagnetic acoustic transducers may not provide a magnetic field that is as strong as desired for generating acoustic waves with materials that have lower connectivities as compared to metals and alloys. For example, the different advantageous embodiments recognize and take into account that currently used electromagnetic acoustic transducers may have difficulties in generating desired acoustic waves in test objects such as composite structures.

The different advantageous embodiments recognize and take into account that desired acoustic waves may be generated when the magnetic field is increased to a high enough level. Thus, the different advantageous embodiments provide a method and apparatus for generating acoustic waves in an object. In one advantageous embodiment, an apparatus comprises a conductive material and a current inducer. The conductive material is configured to generate a magnetic field. The magnetic field has magnetic flux lines that are substantially fixed. Further, the current inducer is configured to cause an electric current in the test objects that interacts with the magnetic field. The frequency of the electric current generates an acoustic test wave in the test object.

Figure 1:
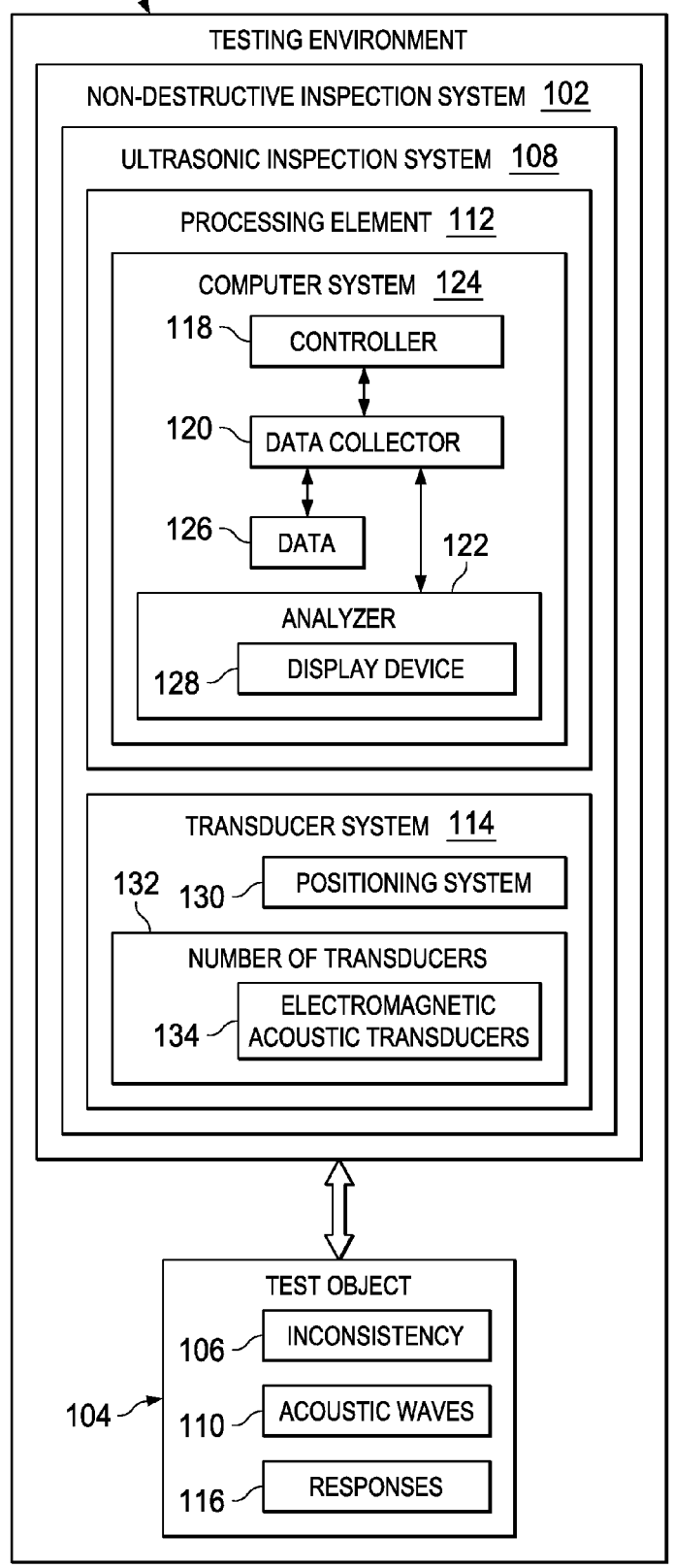
FIG. 1 is an illustration of a block diagram of a testing environment in accordance with an advantageous embodiment.

With reference now to the figures and, in particular, with reference to FIG. 1, an illustration of a block diagram of a testing environment is depicted in accordance with an advantageous embodiment. In this illustrative example, testing environment 100 includes non-destructive inspection (NDI) system 102. As depicted, non-destructive inspection (NDI) system 102 may be used to perform tests on test object 104. Test object 104 may take a number of different forms. For example, test object 104 may be selected from one of a skin panel, a composite skin panel, a metal skin panel, a fuselage, a wing, an engine housing, a composite structure, an aircraft, a spacecraft, a submarine, a mold, and/or other suitable objects.

For example, non-destructive inspection system 102 may be used to determine whether inconsistency 106 is present in test object 104.

In this illustrative example, non-destructive inspection system 102 takes the form of ultrasonic inspection system 108. Ultrasonic inspection system 108 may be used to generate and detect acoustic waves 110 in test object 104. In these illustrative examples, ultrasonic inspection system 108 comprises processing element 112 and transducer system 114.

Processing element 112 is configured to cause transducer system 114 to generate acoustic waves 110 in test object 104. Further, processing element 112 is also configured to cause transducer system 114 to detect responses 116 generated from acoustic waves 110.

In this illustrative example, processing element 112 comprises controller 118, data collector 120, and analyzer 122. Controller 118, data collector 120, and analyzer 122 may be implemented using hardware, software, or a combination of the two. As depicted, the components in processing element 112 may be implemented using computer system 124. Computer system 124 is one or more computers. When more than one computer is present, these computers may communicate with each other through a medium such as a network.

Data collector 120 is configured to record and store data 126 for at least one of acoustic waves 110 generated and responses 116 detected in response to acoustic waves 110.

As used herein, the phrase "at least one of", when used with a list of items, means different combinations of one or more of the listed items may be used and only one of each item in the list may be needed. For example, "at least one of item A, item B, and item C" may include, for example, without limitation, item A, or item A and item B. This example also may include item A, item B, and item C, or item B and item C. This data may include, for example, without limitation, amplitudes of acoustic waves 110, amplitudes for responses 116, times at which acoustic waves 110 were transmitted, and times at which responses 116 were received as well as other suitable types of data.

Analyzer 122 is configured to analyze data 126 and may determine whether inconsistency 106 is present. Further, analyzer 122 may display data 126 on display device 128 in computer system 124.

As depicted, transducer system 114 is implemented using hardware and comprises positioning system 130 and number of transducers 132. Positioning system 130 may be a fixed system or may be a moveable system. When positioning system 130 is a moveable system, positioning system 130 may be a robotic or some other suitable automated system under the control of controller 118. Number of transducers 132, in these illustrative examples, takes the form of electromagnetic acoustic transducers 134.

Figure 2:
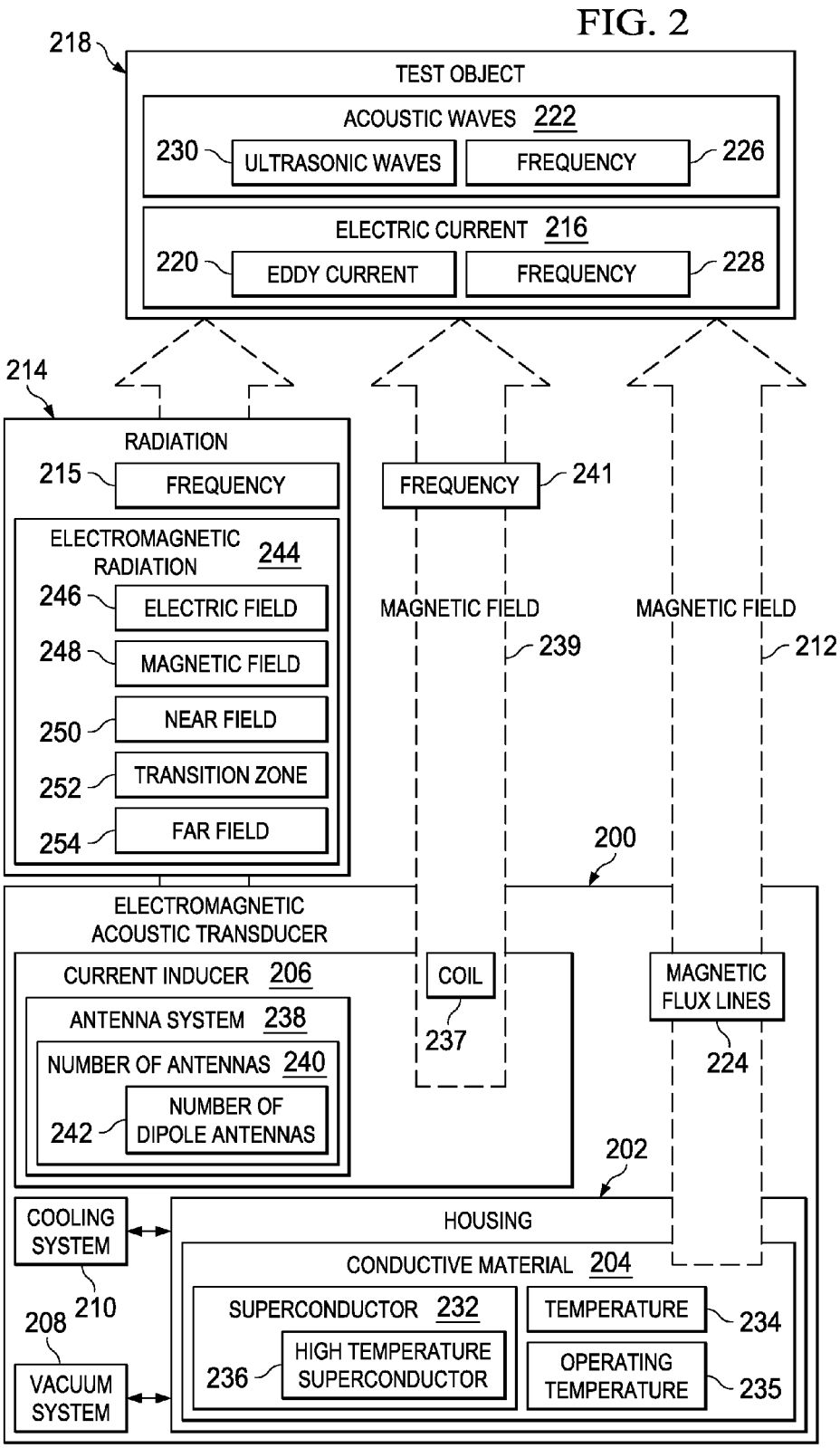
FIG. 2 is an illustration of a block diagram of an electromagnetic acoustic transducer in accordance with an advantageous embodiment.

Turning now to FIG. 2, an illustration of a block diagram of an electromagnetic acoustic transducer is depicted in accordance with an advantageous embodiment. In this illustrative example, electromagnetic acoustic transducer 200 is an example of an electromagnetic acoustic transducer within electromagnetic acoustic transducers 134 in FIG. 1.

In these illustrative examples, electromagnetic acoustic transducer 200 may comprise housing 202, conductive material 204, current inducer 206, vacuum system 208, and cooling system 210. In these illustrative examples, conductive material 204, current inducer 206, vacuum system 208, and cooling system 210 are associated with housing 202.

When one component is "associated" with another component, the association is a physical association in these depicted examples. For example, a first component may be considered to be associated with a second component by being secured to the second component, bonded to the second component, mounted to the second component, welded to the second component, fastened to the second component, and or connected to the second component in some other suitable manner. The first component also may be connected to the second component using a third component. The first component also may be considered to be associated with the second component by being formed as part of and or an extension of the second component.

In this illustrative example, conductive material 204 is a magnetic field source and is configured to generate magnetic field 212. Current inducer 206 is configured to generate radiation 214 with frequency 215. Radiation 214 causes electric current 216 to flow within test object 218 in this illustrative example. In particular, electric current 216 may take the form of eddy current 220.

When electric current 216 interacts with magnetic field 212, acoustic waves 222 are generated. As depicted, frequency 228 is derived from frequency 215 of radiation 214 in these illustrative examples. In other words, frequency 228 is determined by frequency 215. In the illustrative example, frequency 228 is the same as frequency 215. This change results in acoustic waves 222 with frequency 226. In these illustrative examples, controller 118 in FIG. 1 is configured to cause current inducer 206 to generate electric current 216 with frequency 228 that causes acoustic waves 222 to have frequency 226, which is a desired frequency in these illustrative examples.

In these illustrative examples, acoustic waves 222 take the form of ultrasonic waves 230. Frequency 226 of acoustic waves 222 is selected by selecting frequency 228 for radiation 214. Frequency 226 of acoustic waves 222 may be, for example, from about 20 kHz to about 20 MHz. Of course, the frequencies used may depend on the particular implementation.

Conductive material 204 is configured to generate magnetic field 212 having magnetic flux lines 224 that are substantially fixed. When magnetic flux lines 224 are substantially fixed for conductive material 204, conductive material 204 is a trapped field conductive material. Magnetic flux lines 224 are substantially fixed relative to electromagnetic acoustic transducer 200. A permanent magnet consists of magnetized domains that are oriented in the same direction when exposed to an external magnetic field. In contrast, a trapped field conductive material has no magnetized parts until the trapped field conductive material is exposed to an external field. After exposure to an external magnetic field, the trapped field conductive material magnetizes and can maintain part of its magnetization after the external field is removed.

Conductive material 204 is selected as a material having substantially zero electrical resistance at a selected temperature or range of temperatures. In these illustrative examples, conductive material 204 takes the form of superconductor 232. Superconductor 232 is configured to have substantially zero electrical resistance when temperature 234 of superconductor 232 is reduced to being less than or equal to operating temperature 235. In these illustrative examples, conductive material 204 may be selected from one of bismuth strontium calcium copper oxide, yttrium barium copper oxide (YBCO), magnesium diboride, lanthanum barium copper oxide, bis-ethylenedithio-tetrathiafulvalene, and other suitable materials. In the illustrative examples, yttrium in yttrium barium copper oxide may be replaced materials, such as, for example, gadolinium, dysprosium, neodymium, samarium, europium, and other rare earths materials. For example, gadolinium barium copper oxide, dysprosium barium copper oxide, neodymium barium copper oxide, samarium barium copper oxide, and europium barium copper oxide may be used. The use of these materials also may result in conductive material 204 producing a desired trapped flux.

The critical temperature of superconductor 232 is the temperature at and below which the electrical resistance becomes zero. Operating temperature 235 of superconductor 232 is at or below the critical temperature in these illustrative examples.

Superconductor 232 may be selected as high temperature superconductor 236. High temperature superconductor 236 is comprised of a conductive material that has substantially zero resistance at temperatures greater than about 30 degrees Kelvin.

In these illustrative examples, vacuum system 208 and cooling system 210 are configured for use in maintaining temperature 234 of conductive material 204 at a level at which substantially zero resistance is present and at a level at which magnetic flux lines 224 in magnetic field 212 are substantially fixed. In these illustrative examples, vacuum system 208 is configured to create a vacuum around conductive material 204. This vacuum along with cooling system 210 may maintain temperature 234 of conductive material 204 at a desired temperature.

By being substantially fixed, magnetic flux lines 224 remain substantially in the same place when conductive material 204 does not move. In these illustrative examples, current inducer 206 comprises at least one of coil 237 and antenna system 238. Coil 237 is configured to generate magnetic field 239 with frequency 241 in a manner that causes electric current 216 to flow in test object 218 with frequency 228. Coil 237 may be any coil that is capable of generating magnetic field 239 in a way to cause the flow of electric current 216 within test object 218.

As depicted, antenna system 238 has number of antennas 240. As used herein, a "number", when used with reference to items, means one or more items. For example, "number of antennas 240" is one or more antennas.

Number of antennas 240 may take various forms. For example, number of antennas 240 may be number of dipole antennas 242. Antenna system 238 is configured to generate radiation 214 in the form of electromagnetic radiation 244. Electromagnetic radiation 244 has electric field 246 and magnetic field 248.

In these illustrative examples, electromagnetic radiation 244 may have near field 250, transition zone 252, and far field 254. Near field 250 is the desired portion of electromagnetic radiation 244 that encompasses test object 218 in the depicted examples. In other words, near field 250 encompasses at least a portion of test object 218 such that electric current 216 flows in test object 218. Near field 250 is the portion of electromagnetic radiation 244 that is within about one wavelength in distance from antenna system 238.

In these illustrative examples, if the electrical conductivity of the test sample is anisotropic or contains acicular inclusions such as fibers in which the electrical conductivity of the acicular inclusion is greater than the rest of the material, electric field 246 is preferably configured to be a larger component in electromagnetic radiation 244 as compared to magnetic field 248 for near field 250 of electromagnetic radiation 244.

In these illustrative examples, electric field 246 is the component of electromagnetic radiation 244 that causes electric current 216 to flow in test object 218. Otherwise, magnetic field 248 is preferably configured to be a larger component in electromagnetic radiation 244 as compared to electric field 246 for near field 250 of electromagnetic radiation 244.

Further, if test object 218 is comprised of ferromagnetic material, acoustic waves 222 may be generated using magnetostriction. In magnetostriction, a ferromagnetic material has a dimensional change when an external magnetic field is applied. By changing the field with some frequency, the magnetostriction may cause a disturbance that propagates as an acoustic wave.

In these illustrative examples, conductive material 204 is not a permanent magnet. As a result, magnetic field 212 is induced in conductive material 204 prior to using electromagnetic acoustic transducer 200.

Figure 3:
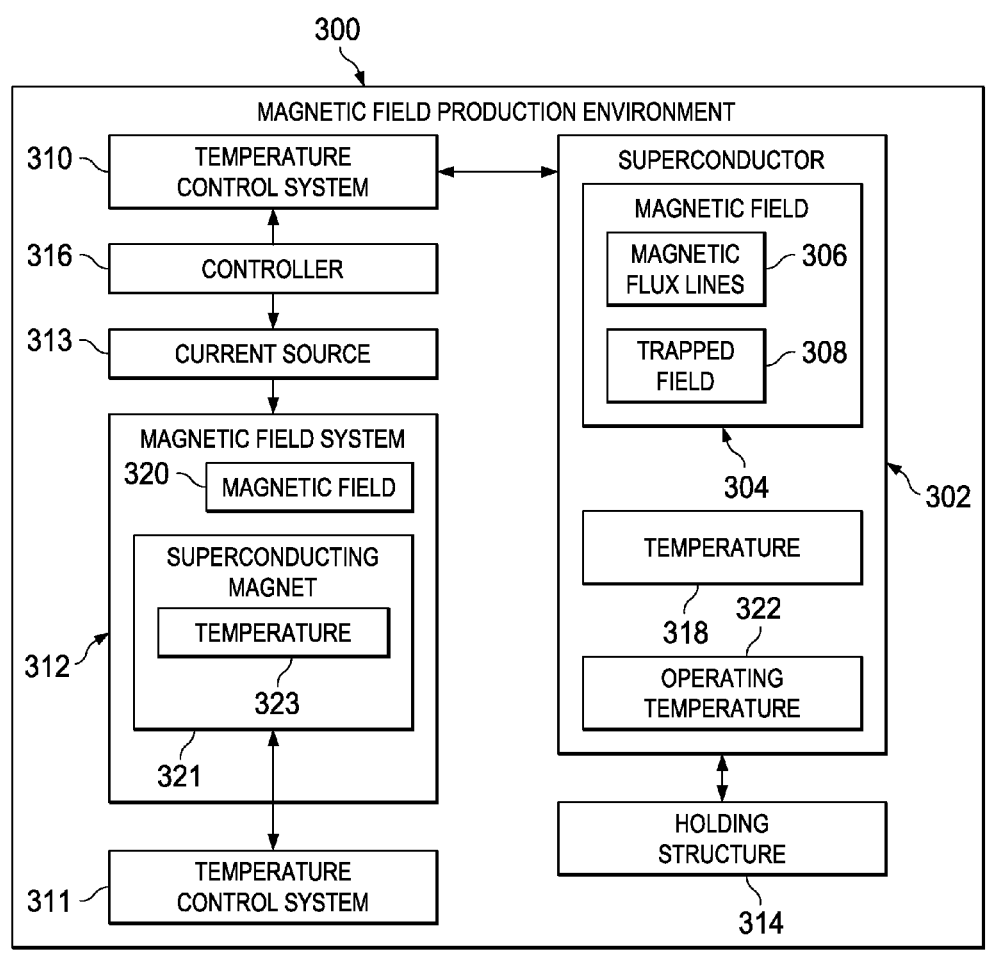
FIG. 3 is an illustration of a block diagram of a magnetic field production environment in accordance with an advantageous embodiment.

Turning now to FIG. 3, an illustration of a block diagram of a magnetic field production environment is depicted in accordance with an advantageous embodiment. Magnetic field production environment 300 is configured to cause superconductor 302 to generate magnetic field 304 with substantially fixed magnetic flux lines 306. More specifically, magnetic field production environment 300 may be used to cause superconductor 302 to have trapped field 308.

As depicted, magnetic field production environment 300 includes temperature control system 310, temperature control system 311, magnetic field system 312, current source 313, holding structure 314, and controller 316. Temperature control system 310 is configured to control temperature 318 of superconductor 302. Magnetic field system 312 is configured to generate magnetic field 320. As illustrated, magnetic field system 312 may be implemented using superconducting magnet 321. This magnetic field is a second magnetic field. Magnetic field 320 is generated prior to superconductor 302 generating the first magnetic field, magnetic field 304. Holding structure 314 is configured to hold superconductor 302. In particular, holding structure 314 is configured to hold superconductor 302 in a fixed position relative to magnetic field system 312.

In this illustrative example, temperature control system 310 is configured to change temperature 318 of superconductor 302 to a temperature greater than operating temperature 322. Operating temperature 322 is a temperature at which superconductor 302 has substantially zero resistance to an electric current. Further, operating temperature 322 may also be the temperature at which superconductor 302 has sufficient current density to trap magnetic field 304.

In these illustrative examples, the critical temperature may be the temperature at which superconductor 302 has substantially zero resistance to an electric current and has a current density that is substantially equal to zero. Operating temperature 322 is below the critical temperature for superconductor 302 so that a non-zero current density may exist to support the trapped field. Under these conditions, superconductor 302 may be a trapped field superconductor.

With temperature 318 greater than operating temperature 322, controller 316 causes magnetic field system 312 to generate magnetic field 320. In particular, controller 316 may control current source 313 to send an electric current to operate superconducting magnet 321 in magnetic field system 312 to generate magnetic field 320. In these illustrative examples, current source 313 is an alternating current source.

In this illustrative example, temperature control system 311 is configured to cool magnetic field system 312. In particular, temperature control system 311 may maintain temperature 323 of superconducting magnet 321 at an operating temperature at which superconducting magnet 321 generates magnetic field 320 at a desired level.

While magnetic field 320 is held constant, controller 316 causes temperature control system 311 to lower temperature 318 of superconductor 302. In particular, temperature 318 is lowered to or below operating temperature 322 of superconductor 302.

When temperature 318 reaches or moves below operating temperature 322, controller 316 causes magnetic field system 312 to reduce magnetic field 320. In these illustrative examples, magnetic field 320 may be about 10 Teslas. Magnetic field 320 may vary from about 2 Teslas to about 15 Teslas in some illustrative examples. Of course, other values for magnetic field 320 may be present depending on the particular implementation.

The rate at which magnetic field 320 is reduced may depend on magnetic field system 312. For example, superconducting magnet 321 may have superconducting wires. The rate at which magnetic field 320 may be reduced is a rate that avoids quenching the superconducting wires in superconducting magnet 321. Quenching may occur when the superconducting wires enter a resistive state and no longer provide magnetic operation. This rate may be, for example, about 1 Tesla per 100 seconds. Of course, the rate may vary depending on superconducting magnet 321.

At this point, superconductor 302 may be used in an electromagnetic acoustic transducer such as electromagnetic acoustic transducer 200 in FIG. 2. In some illustrative examples, the entire electromagnetic acoustic transducer may be cooled rather than removing superconductor 302 from the electromagnetic acoustic transducer.

The illustrations of testing environment 100 in FIG. 1, electromagnetic acoustic transducer 200 in FIG. 2, and magnetic field production environment 300 in FIG. 3 are not meant to imply physical or architectural limitations to the manner in which an advantageous embodiment may be implemented. Other components in addition to and/or in place of the ones illustrated may be used. Some components may be unnecessary. Also, the blocks are presented to illustrate some functional components. One or more of these blocks may be combined, divided, or combined and divided into different blocks when implemented in an advantageous embodiment.

For example, data collector 120 and analyzer 122 may be combined as a single component. In still other illustrative examples, vacuum system 208 may be omitted or may be implemented as part of cooling system 210. In still other illustrative examples, current inducer 206 may be attached to or incorporated as part of housing 202 and/or another structure depending on the particular implementation. In another example, holding structure 314 may be part of temperature control system 310.

In yet another example, although conductive material 204 has been illustrated as superconductor 232, more than one superconductor may be used. In other words, more than one type of superconductor may be used and more than one superconductor structure may be used. Different types of superconductors and superconductor structures in addition to superconductor 232 may be employed to provide different orientations and patterns of magnetic field 212.

With reference next to FIG. 4, an illustration of a cross-sectional view of an electromagnetic acoustic transducer is depicted in accordance with an advantageous embodiment. In this illustrative example, electromagnetic acoustic transducer 400 is an example of one implementation for electromagnetic acoustic transducer 200 in FIG. 2 and electromagnetic acoustic transducers 134 in FIG. 1.

In this cross-sectional view, electromagnetic acoustic transducer 400 has distance 402 from test object 404. In other words, electromagnetic acoustic transducer 400 is not in physical contact with test object 404.

As depicted, electromagnetic acoustic transducer 400 includes conductive material 405. In this example, conductive material 405 takes the form of high temperature superconductor 406.

High temperature superconductor 406 has magnetic flux lines that are fixed. In other words, high temperature superconductor 406 has a trapped field that provides a magnetic field in the direction of arrow 407. In this illustrative example, arrow 407 is along a center line for high temperature superconductor 406.

High temperature superconductor 406 has the shape of a cylinder with a circular cross section. Of course, high temperature superconductor 406 may have other cross-sectional shapes. For example, the shape may be a square, a pentagon, a hexagon, or some other suitable shape.

As depicted, high temperature superconductor 406 is in contact with structure 408. More specifically, high temperature superconductor 406 is in physical and thermal contact with structure 408. In other words, heat may be conducted between high temperature superconductor 406 and structure 408.

In this illustrative example, structure 408 is configured to hold high temperature superconductor 406 within electromagnetic acoustic transducer 400. Structure 408 may be comprised of any material that conducts heat. As depicted, structure 408 is comprised of copper. Clamp 410 holds high temperature superconductor 406 in place with respect to structure 408.

In these illustrative examples, structure 408 is connected to cooling system 416. In this illustrative example, cooling system 416 comprises cryocooler 418. More specifically, cooling system 416 is thermally connected to cold head 412 of cryocooler 418.

Cryocooler 418 may be implemented using any device configured to maintain the temperature of high temperature superconductor 406 at an operating temperature or below the operating temperature for high temperature superconductor 406 in these illustrative examples. As depicted, cryocooler 418 may be mounted on plate 420. Power connector 421 may be connected to a power source to provide power to operate cryocooler 418. Alternatively, cryocooler 418 may be, for example, a container with liquid nitrogen.

Additionally, electromagnetic acoustic transducer 400 has housing 422. Housing 422 has walls 424 and end cap 425 that define cavity 426 in which high temperature superconductor 406, clamp 410, and a portion of cold head 412 are located.

End cap 425 is removable. Removal of end cap 425 allows access to cavity 426. Cold head 412 extends into cavity 426 through opening 428 in walls 424.

Cavity 426 may be a vacuum space in which a vacuum is generated within housing 422. Further, insulation 429 may be present within cavity 426. Insulation 429 is configured to reduce the transfer of heat between high temperature superconductor 406, walls 424, and end cap 425. Insulation 429 may take the form of multi-layer insulation. Insulation 429 may be, for example, sheets of aluminized biaxially-oriented polyethylene terephthalate or other suitable types of insulation.

In this illustrative example, vacuum pump 430 also is mounted on plate 420. Vacuum pump 430 is connected to housing 422 by tube 432. Once a vacuum has been established in cavity 426, valve 434 may be closed and vacuum pump 430 may be disconnected from tube 432. In these illustrative examples, vacuum pump 430 and insulation 429 may reduce heat from reaching cold head 412 and high temperature superconductor 406.

As depicted, current inducer 436 in electromagnetic acoustic transducer 400 takes the form of coil 437 and/or antenna system 438 in these illustrative examples. As depicted, current inducer 436 may have elements 439 and support structure 440. When current inducer 436 takes the form of coil 437, elements 439 may be windings in a coil for coil 437. When current inducer 436 takes the form of antenna system 438, elements 439 may take the form of antenna elements. Additionally, current inducer 436 has wires 442 that may be connected to a radio frequency signal generator.

Support structure 440 with elements 439 is located between test object 404 and end cap 425. In this illustrative example, antenna system 438 is not connected to housing 422. Of course, in other illustrative examples, support structure 440 for antenna system 438 may be connected to housing 422, plate 420, or some other structure for positioning antenna system 438.

In this illustrative example, antenna system 438 has distance 444 to high temperature superconductor 406. Distance 444 may be fixed or adjustable depending on the particular implementation.

Turning now to FIG. 5, an illustration of an implementation for a magnetic field and production environment is depicted in accordance with an advantageous embodiment. In this illustrative example, magnetic field production environment 500 is shown in a cross-sectional view and is an example of one implementation for magnetic field production environment 300 in FIG. 3.

As depicted, magnetic field production environment 500 comprises magnetic field system 502 which takes the form of superconducting magnet 503. Additionally, in this illustrative example, temperature control system 504 includes holding structure 506 that is configured to high temperature superconductor 406 in a fixed position while a magnetic field with substantially fixed magnetic flux lines is generated in high temperature superconductor 406.

In this illustrative example, holding structure 506 with high temperature superconductor 406 is placed inside of bore 510 of superconducting magnet 503. Bore 510 may have a temperature that is substantially the same as the ambient temperature in these illustrative examples. In other words, the temperature in bore 510 is independent of the temperature in the windings within superconducting magnet 503.

In these illustrative examples, bore 510 may have a diameter greater than about one inch. Of course, the diameter may be any diameter that may be configured to receive high temperature superconductor 406 and any components holding high temperature superconductor 406, such as holding structure 506.

In this illustrative example, high temperature superconductor 406 initially has a temperature greater than its operating temperature. Superconducting magnet 503 is operated to generate a magnetic field in bore 510. The magnetic field is increased to a magnetizing value.

As depicted, the magnetizing value is the strength of the magnetic field that high temperature superconductor 406 is exposed to as the temperature of high temperature superconductor 406 is reduced to an operating temperature. Further, in these illustrative examples, the magnetizing value may be greater than the desired value for the trapped magnetic field in high temperature superconductor 406.

The magnetic field generated by superconducting magnet 503 is held constant while the temperature of high temperature superconductor 406 is lowered by temperature control system 504. The temperature may be lowered to the operating temperature of high temperature superconductor 406 or to an even lower temperature depending on the particular implementation. Once high temperature superconductor 406 reaches the operating temperature, the magnetic field generated by superconducting magnet 503 is reduced. In another illustrative example, rather than ramping or reducing the magnetic field generated by superconducting magnet 503, high temperature superconductor 406 may be physically removed from bore 510.

Thereafter, high temperature superconductor 406 may be moved in housing 422 in electromagnetic acoustic transducer 400 and placed on structure 408 and held in place with clamp 410 in FIG. 4.

The movement of high temperature superconductor 406 may be performed in a vacuum, dry atmosphere, or some other suitable environment. The transfer is performed in a manner that avoids increasing the temperature of high temperature superconductor 406 such that the temperature of high temperature superconductor 406 does not increase in a manner that the magnetic flux lines in the magnetic field generated by high temperature superconductor 406 are no longer substantially fixed.

In a superconductor, the critical current density increases as the temperature decreases from a current density of zero at the critical temperature to some value at absolute zero. In these illustrative examples, critical current density is when the current density is strong enough to produce a non-zero electrical resistivity in the superconductor. The magnitude of the trapped field will be approximately proportional to the current density. As a result, as operating temperature decreases, the strength of the trapped field increases. However, the trapped field cannot be higher than the magnetizing field in the illustrative examples. In some illustrative examples, heat capacity is less as the temperature decreases. As a result, the superconductor may quench more easily than desired. As a result, a superconductor with a higher operating temperature is desirable.

Temperature control system 504 may be implemented in a number of different ways. For example, temperature control system 504 may include a helium gas source that flows to high temperature superconductor 406 through holding structure 506. Alternatively, liquid may be used. For example, without limitation, the liquids used in temperature control system 504 may be liquid helium, liquid nitrogen, liquid hydrogen, liquid neon, liquid oxygen, and combinations of these liquids.

In other illustrative examples, temperature control system 504 may comprise a liquid helium source in which helium 507 flows in contact with at least one of holding structure 506 and high temperature superconductor 406. In other examples, a cryocooler may be placed in thermal contact with at least one of holding structure 506 and high temperature superconductor 406.

In this illustrative example, superconducting magnet 503 may be constructed from a number of different materials. For example, superconducting magnet 503 may be constructed from NbTi or $Nb_3Nn$. Superconducting magnet 503, for example, without limitation, may be cooled to an operating temperature through liquid helium, a super fluid helium cryostat, or a cryocooler.

In these illustrative examples, the magnetic field inside of bore 510 of superconducting magnet 503 is in the direction of arrow 514 in center line 516 of bore 510. As a result, the magnetic field generated by high temperature superconductor 406 is also along the direction of arrow 514.

In some illustrative examples, electromagnetic acoustic transducer 400 in FIG. 4 with high temperature superconductor 406 may be placed in bore 510, or superconducting magnet 503 may be placed around electromagnetic acoustic transducer 400. This type of placement avoids the need to transfer high temperature superconductor 406 from holding structure 506 to housing 422.

As a result, the need for placing electromagnetic acoustic transducer 400 in a vacuum chamber to transfer high temperature superconductor 406 from holding structure 506 to housing 422 may be avoided. In this illustrative example, only housing 422 may need to be within bore 510. Other components such as cryocooler 418 and antenna system 438 in FIG. 4 may be on the fringe or outside of bore 510.

In still another illustrative example, high temperature superconductor 406 may be exposed to a series of pulses of a magnetic field generated by a magnet. In these illustrative examples, superconducting magnet 503 is replaced with a non-superconducting magnet when a series of pulses are generated. For pulsed fields, the magnet used is not superconducting magnet 503 in the illustrative examples. However, superconducting magnet 503 could be used in some illustrative examples.

In this illustrative example, high temperature superconductor 406 may be at the operating temperature for high temperature superconductor 406 or substantially close to the operating temperature for high temperature superconductor 406 when the pulses of the magnetic field are delivered to high temperature superconductor 406 from a magnet used in place of superconducting magnet 503.

When pulses of a magnetic field are used to produce the trapped field in high temperature superconductor 406, the magnetic field of the pulses are higher than when the field from superconducting magnet 503 can be held steady and the temperature of high temperature superconductor 406 is reduced to at or below an operating temperature for high temperature superconductor 406. These two conditions are used to obtain a trapped field in high temperature superconductor 406.

Turning now to FIG. 6, an illustration of an antenna is depicted in accordance with an advantageous embodiment. In this illustrative example, antenna 600 is an example of an implementation of an antenna in antenna system 438 in FIG. 4. In this illustrative example, antenna 600 takes the form of dipole antenna array 602. Antenna 600 includes antenna elements 604, 606, 608, 610, 612, 614, 616, and 618. In this illustrative example, the letter "A" refers to one terminal of a radio frequency signal generator and the letter "B" refers to another terminal on the radio frequency signal generator. These letters identify the terminals to which different antenna elements are connected. In this illustrative example, the connection and arrangement of antenna elements 604, 606, 608, 610, 612, 614, 616, and 618 generates an electric field pattern that has four rows of excitation. Each row is about 180 degrees out of phase with another row.

As depicted, antenna element 604 and antenna element 606 form row 620. Antenna element 608 and antenna element 610 form row 622. Antenna element 612 and antenna element 614 form row 624, and antenna element 616 and antenna element 618 form row 626.

Of course, this illustration of antenna 600 is only one example and any number of elements may be used in this illustrative configuration. Of course, other configurations may be used with other types of antenna geometries.

Figure 7:
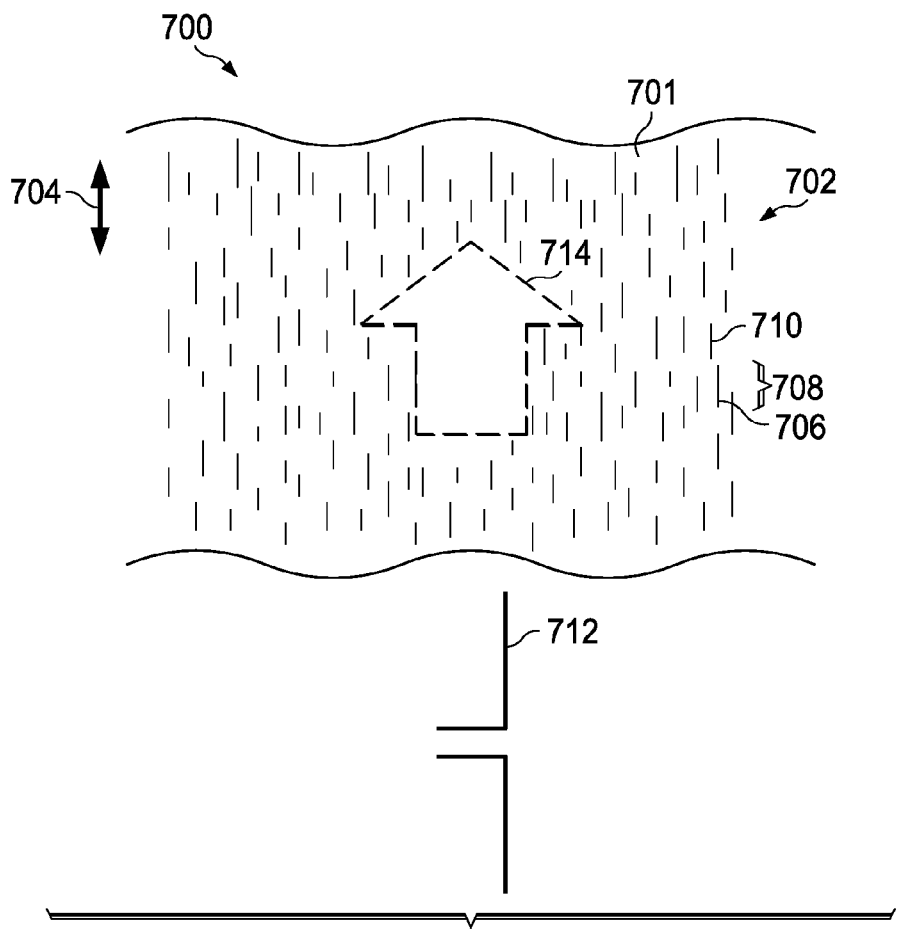
FIG. 7 is an illustration of an electric field aligned with a test object in accordance with an advantageous embodiment.

Turning next to FIG. 7, an illustration of an electric field aligned with a test object is depicted in accordance with an advantageous embodiment. In this illustrative example, test object 700 has layer 701, which is comprised of carbon fibers 702. In these illustrative examples, carbon fibers 702 are aligned in the direction of arrow 704.

Carbon fibers 702 are electrically conductive along their fiber length. For example, carbon fiber 706 is conductive along length 708. The different advantageous embodiments recognize and take into account that the conductivity from fiber to fiber may not be as great as desired. For example, conductivity from carbon fiber 706 to carbon fiber 710 may require more current than desired to produce a large enough signal to detect an inconsistency.

In the illustrative examples, antenna 712 may be configured to generate electromagnetic radiation with an electric field having electric field vector 714 that is substantially aligned in the direction of carbon fibers 702. In this manner, electromagnetic radiation generated by antenna 712 may cause a current to flow along each carbon fiber in carbon fibers 702 in the direction of arrow 704.

Further, other layers in test object 700 may have carbon fibers with a different orientation. Antenna 712 may be configured to selectively cause a current in layers having an orientation that is aligned with electric field vector 714. This current may then interact with a magnetic field from a superconductor to cause a Lorenz force that results in an acoustic wave within test object 700.

The illustrations of components in FIGS. 4-7 may be combined with the components illustrated in FIGS. 1-3, used with components in FIGS. 1-3, or a combination of the two. Additionally, some of the components illustrated in FIGS. 4-7 may be illustrative examples of how components shown in block form in FIGS. 1-3 can be implemented as physical structures.

Further, the illustrations of electromagnetic acoustic transducer 400 in FIG. 4, magnetic field production environment 500 in FIG. 5, antenna 600 in FIG. 6, and test object 700 in FIG. 7 are not meant to imply physical or architectural limitations to the manner in which an advantageous embodiment may be implemented. These components are illustrations of one manner in which an advantageous embodiment may be implemented.

Figure 8:
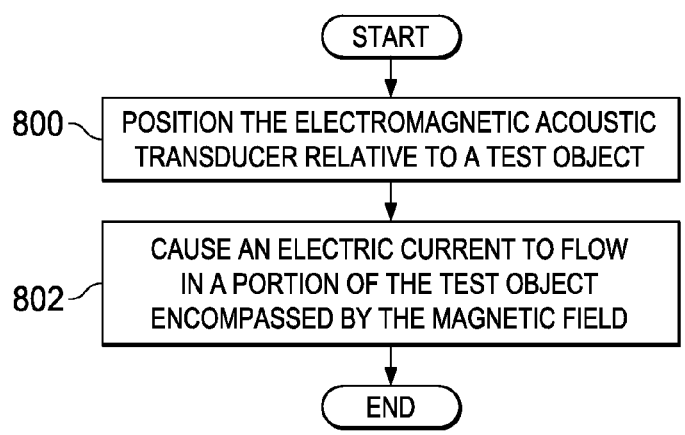
FIG. 8 is an illustration of a flowchart of a process for operating an electromagnetic acoustic transducer in accordance with an advantageous embodiment.

Turning now to FIG. 8, an illustration of a flowchart of a process for operating an electromagnetic acoustic transducer is depicted in accordance with an advantageous embodiment. The process begins by positioning the electromagnetic acoustic transducer relative to a test object (operation 800). This positioning does not require physical contact with the test object. The electromagnetic acoustic transducer has a conductive material configured to generate a magnetic field that encompasses at least a portion of the test object when the electromagnetic acoustic transducer is positioned relative to the test object. The magnetic field has magnetic flux lines that are fixed.

The process then causes an electric current to flow in a portion of the test object encompassed by the magnetic field (operation 802) in which the electric current interacts with the magnetic field to generate an acoustic wave in the test object.

Detection of an acoustic wave using an electromagnetic acoustic transducer may occur by monitoring a change in a magnetic field, an electric field, or both in response to the response of the acoustic wave that moves through a magnetic field and generates a current. A current has an electric field and a magnetic field. The electric field, the magnetic field, or both may be measured. In these illustrative examples, this measurement may be made through the current inducer which is a coil, antenna, or some other suitable device.

Turning now to FIG. 9, an illustration of a flowchart of a process for preparing a superconductor for use in an electromagnetic acoustic transducer is depicted in accordance with an advantageous embodiment. This process may be implemented in magnetic field production environment 300 in FIG. 3 or the example illustrated by magnetic field production environment 500 in FIG. 5.

The process begins by changing a temperature of the superconductor to greater than an operating temperature for the superconductor (operation 900). The process then generates a magnetic field around the superconductor held in a fixed position while the superconductor has a temperature greater than the operating temperature (operation 902). The fixed position of the superconductor is relative to the magnetic field generator generating the magnetic field. In other words, the superconductor does not move relative to the magnetic field. The process then decreases the temperature of the superconductor to equal to or less than the operating temperature while the magnetic field is present (operation 904), with the process terminating thereafter.

With reference next to FIG. 10, an illustration of a flowchart of a process for preparing a superconductor for use in an electromagnetic acoustic transducer is depicted in accordance with an advantageous embodiment. This process may be implemented in magnetic field production environment 300 in FIG. 3 or in the example illustrated by magnetic field production environment 500 in FIG. 5.

The process begins by changing the temperature of the superconductor to a temperature that is substantially the operating temperature for the superconductor (operation 1000). Thereafter, the process generates a series of pulses of a magnetic field around the superconductor held in a fixed position while the superconductor has a temperature that is substantially the operating temperature for the superconductor (operation 1002). The temperature may be, for example, plus or minus 10 Kelvin from the operating temperature. In these illustrative examples, the amplitude of the pulses is higher than the desired trapped field. The length of a pulse may be in a range of several milliseconds to several tenths of a second. As depicted, about 5 to about 10 pulses are used. Other numbers of pulses may be used depending on the implementation.

Turning now to FIG. 11, an illustration of a flowchart of a process for generating an acoustic wave in a composite material is depicted in accordance with an advantageous embodiment. The process illustrated in FIG. 11 may be implemented using transducer system 114 in FIG. 1.

The process begins by identifying an orientation of fibers in a number of layers of composite material in a test object (operation 1100). In these illustrative examples, one or more layers in the composite material may have the same orientation. Further, other layers may have a different orientation depending on the design of the test object.

The process configures the antenna system to generate electromagnetic radiation such that the electromagnetic radiation has an electric field vector that is in the direction of the fibers (operation 1102). The process then generates the electromagnetic radiation (operation 1104), with the process terminating thereafter. In operation 1104, the electric field component of the electromagnetic radiation causes an electric current to flow in the fibers. This electric current interacts with the magnetic field generated by the superconductor to cause an acoustic wave in the test object.

The flowcharts and block diagrams in the different depicted embodiments illustrate the architecture, functionality, and operation of some possible implementations of apparatuses and methods in an advantageous embodiment. In this regard, each block in the flowcharts or block diagrams may represent a module, segment, function, and/or a portion of an operation or step.

In some alternative implementations of an advantageous embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, operation 900 assumes that the temperature of the superconductor is below the operating temperature. If the temperature of the superconductor is greater than the operating temperature, operation 900 may be omitted.

Thus, the different advantageous embodiments provide an ability to increase the magnetic field generated by an electromagnetic acoustic transducer in a manner that allows for acoustic waves to be generated in materials that have lower conductivities as compared to a metal. For metallic materials, the advantageous embodiments allow for an electromagnetic acoustic transducer to be used at greater standoff distances or to have the capability of detecting smaller inconsistencies as compared to a currently available electromagnetic acoustic transducer.

Figure 12:
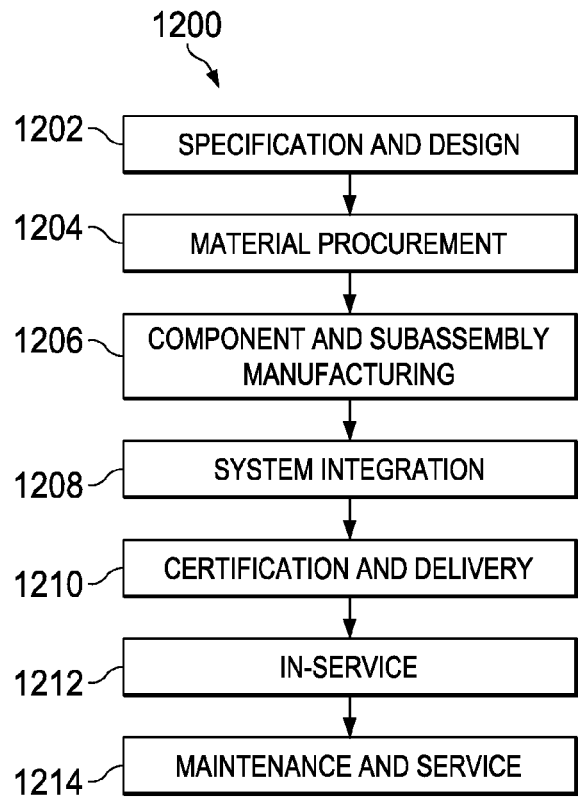
FIG. 12 is an illustration of an aircraft manufacturing and service method in accordance with an advantageous embodiment.
Figure 13:
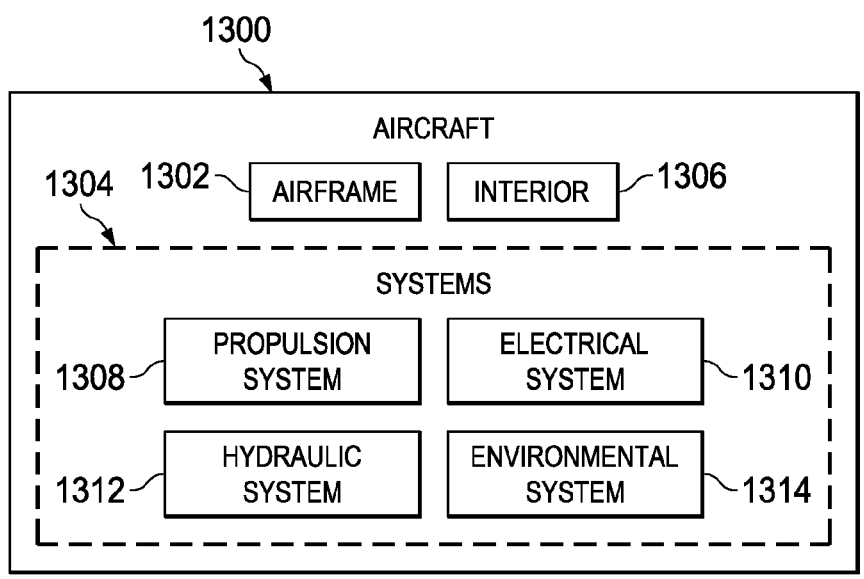
FIG. 13 is an illustration of an aircraft in which an advantageous embodiment may be implemented.

Advantageous embodiments of the disclosure may be described in the context of aircraft manufacturing and service method 1200 as shown in FIG. 12 and aircraft 1300 as shown in FIG. 13. Turning first to FIG. 12, an illustration of an aircraft manufacturing and service method is depicted in accordance with an advantageous embodiment. During preproduction, aircraft manufacturing and service method 1200 may include specification and design 1202 of aircraft 1300 in FIG. 13 and material procurement 1204.

During production, component and subassembly manufacturing 1206 and system integration 1208 of aircraft 1300 in FIG. 13 takes place. Thereafter, aircraft 1300 in FIG. 13 may go through certification and delivery 1210 in order to be placed in service 1212. While in service 1212 by a customer, aircraft 1300 in FIG. 13 is scheduled for routine maintenance and service 1214, which may include modification, reconfiguration, refurbishment, and other maintenance or service.

Each of the processes of aircraft manufacturing and service method 1200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 13, an illustration of an aircraft is depicted in which an advantageous embodiment may be implemented. In this example, aircraft 1300 is produced by aircraft manufacturing and service method 1200 in FIG. 12 and may include airframe 1302 with plurality of systems 1304 and interior 1306. Examples of systems 1304 may include one or more of propulsion system 1308, electrical system 1310, hydraulic system 1312, and environmental system 1314. Any number of other systems may be included. Although an aerospace example is shown, different advantageous embodiments may be applied to other industries, such as the automotive industry.

Apparatuses and methods embodied herein may be employed during at least one of the stages of aircraft manufacturing and service method 1200 in FIG. 12 to inspect aircraft 1300 or parts for aircraft 1300. For example, ultrasonic inspection system 108 in FIG. 1 may be used to perform non-destructive inspections on aircraft 1300 or parts for aircraft 1300 during one or more stages of aircraft manufacturing and service method 1200. The use of a number of the different advantageous embodiments may substantially expedite the assembly of and/or reduce the cost of aircraft 1300.

In one illustrative example, components or subassemblies produced in component and subassembly manufacturing 1206 in FIG. 12 may be fabricated or manufactured in a manner similar to components or subassemblies produced while aircraft 1300 is in service 1212 in FIG. 12. The inspection of these components or subassemblies may be inspected using ultrasonic inspection system 108 in FIG. 1.

One or more apparatus embodiments, method embodiments, or a combination thereof may be utilized during production stages, such as component and subassembly manufacturing 1206 and system integration 1208 in FIG. 12. One or more apparatus embodiments, method embodiments, or a combination thereof may be utilized while aircraft 1300 is in service 1212 and/or during maintenance and service 1214 in FIG. 12. For example, ultrasonic inspection system 108 may be used to inspect aircraft 1300 while in service 1212 and/or during maintenance and service 1214.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   a superconducting magnet configured to generate a first magnetic field around a conductive material as a temperature of the conductive material is lowered to a critical temperature;
   the conductive material configured to generate a second magnetic field, such that the second magnetic field comprises magnetic flux lines that are substantially fixed, the temperature of the conductive material being equal to or less than the critical temperature at which the conductive material comprises a substantially zero electrical resistance; and
   a current inducer configured to cause an electric current to flow in a test object that interacts with the second magnetic field, wherein the electric current has a frequency that generates an acoustic wave in the test object.

2. The apparatus of claim 1 further comprising:
   a cooling system configured to reduce the temperature of the conductive material to equal to or less than the critical temperature at which the conductive material has the substantially zero electrical resistance.

3. The apparatus of claim 2 further comprising:
   a vacuum system configured to create a vacuum around the conductive material.

4. The apparatus of claim 1 further comprising:
   a controller configured to cause the current inducer to generate the electric current with the frequency that causes the acoustic wave to have a desired frequency.

5. The apparatus of claim 1, wherein the electric current is a first electric current and wherein the current inducer comprises:
   an antenna system; and
   an alternating current source connected to the antenna system, wherein the alternating current source generates a second electric current having the frequency that causes the antenna system to transmit a radio frequency signal that cause the first electric current to flow in the test object.

6. The apparatus of claim 1, wherein current inducer comprises:

an antenna system configured to generate a near field that encompasses the test object such that the electric current flows in the test object.

7. The apparatus of claim 6, wherein the antenna system is a dipole antenna array.

8. The apparatus of claim 1, wherein the conductive material and the current inducer form an electromagnetic acoustic transducer.

9. The apparatus of claim 8, wherein the electromagnetic acoustic transducer generates acoustic waves having a frequency from about 20 kHz to about 20 MHz.

10. The apparatus of claim 1, wherein the conductive material has the substantially zero electrical resistance and the temperature that is equal to or less than the critical temperature.

11. The apparatus of claim 10, wherein the critical temperature of the conductive material is above about 30 degrees Kelvin.

12. The apparatus of claim 1, wherein the conductive material is selected from one of a superconductor and a high temperature superconductor.

13. The apparatus of claim 1, wherein the conductive material is selected from one of bismuth strontium calcium copper oxide, yttrium barium copper oxide, magnesium diboride, lanthanum barium copper oxide, bisethylenedithio-tetrathiafulvalene, gadolinium barium copper oxide, dysprosium barium copper oxide, neodymium barium copper oxide, samarium barium copper oxide, and europium barium copper oxide.

14. The apparatus of claim 1, wherein the test object is selected from one of a skin panel, a composite skin panel, a metal skin panel, a fuselage, a wing, an engine housing, a composite structure, an aircraft, a spacecraft, a submarine, and a mold.

15. A method for operating an electromagnetic acoustic transducer, the method comprising:
    positioning the electromagnetic acoustic transducer relative to a test object, wherein a conductive material is configured to generate a magnetic field that encompasses at least a portion of the test object and the magnetic field has magnetic flux lines that are substantially fixed, and the conductive material has a temperature that is equal to or less than a critical temperature at which the conductive material has substantially zero electrical resistance, such that the magnetic field is a first magnetic field and the conductive material is a superconductor;
    generating a second magnetic field around the superconductor held in a fixed position while the temperature of the conductive material is greater than the critical temperature;
    decreasing the temperature of the superconductor to equal to or less than the critical temperature while the second magnetic field is present; and
    causing an electric current to flow in the portion of the test object encompassed by the magnetic field, wherein the electric current interacts with the magnetic field to generate an acoustic wave in the test object.

16. The method of claim 15, wherein causing the electric current to flow in the portion of the test object encompassed by the magnetic field, wherein the electric current interacts with the magnetic field to generate the acoustic wave in the test object comprises:
    generating electromagnetic radiation from an antenna system, wherein a near field encompasses the test object such that the electric current flows in the test object, wherein the electric current interacts with the magnetic field to generate the acoustic wave in the test object.

17. The method of claim 15 further comprising:
    generating a series of pulses of the second magnetic field while the superconductor is substantially at the critical temperature such that the superconductor generates the first magnetic field.

18. The method of claim 15, wherein the critical temperature is greater than about 30 degrees Kelvin.

19. The method of claim 15, the conductive material is being a high temperature superconductor.

20. The method of claim 15, wherein the conductive material is selected from one of bismuth strontium calcium copper oxide, yttrium barium copper oxide, magnesium diboride, lanthanum barium copper oxide, bisethylenedithio-tetrathiafulvalene, gadolinium barium copper oxide, dysprosium barium copper oxide, neodymium barium copper oxide, samarium barium copper oxide, and europium barium copper oxide.

21. The method of claim 15, wherein the test object is selected from one of a skin panel, a composite skin panel, a metal skin panel, a fuselage, a wing, an engine housing, a composite structure, an aircraft, a spacecraft, a submarine, and a mold.

* * * * *